United States Patent [19]

Wisotzki et al.

[11] Patent Number: 4,775,424
[45] Date of Patent: Oct. 4, 1988

[54] DISINFECTING AND CLEANING SYSTEM FOR CONTACT LENSES

[75] Inventors: Klaus-Dieter Wisotzki, Erkrath; Klaus Bansemir, Langenfeld; Jochen Jacobs, Wuppertal; Hans Kruse, Korschenbroich, all of Fed. Rep. of Germany

[73] Assignee: Henkel Kommanditgesellshaft auf Aktien, Duesseldorf, Fed. Rep. of Germany

[21] Appl. No.: 79,743

[22] Filed: Jul. 30, 1987

[30] Foreign Application Priority Data

Jul. 31, 1986 [DE] Fed. Rep. of Germany ....... 3626082

[51] Int. Cl.$^4$ .......................... C11D 7/42; C11D 7/34
[52] U.S. Cl. ........................................ 134/42; 134/26; 252/90; 252/95; 252/105; 252/106; 252/174.12; 252/174.13; 252/174.17; 514/25; 514/714
[58] Field of Search ................... 252/95, 90, 106, 105, 252/174.12, 174.13, 174.17; 134/42, 26; 514/25, 714

[56] References Cited

U.S. PATENT DOCUMENTS

| | | | |
|---|---|---|---|
| 4,259,202 | 3/1981 | Tanaka et al. | 252/106 |
| 4,414,127 | 11/1983 | Fu | 252/95 |
| 4,585,488 | 4/1986 | Giefer | 252/106 |
| 4,670,178 | 6/1987 | Huth et al. | 252/106 |
| 4,683,074 | 7/1987 | Malik et al. | 252/174.17 |

FOREIGN PATENT DOCUMENTS 1099885 4/1981 Canada .
3329922 2/1985 Fed. Rep. of Germany ...... 252/106

Primary Examiner—Asok Pal
Attorney, Agent, or Firm—Ernest G. Szoke; Henry E. Millson, Jr.

[57] ABSTRACT

A two component disinfecting and cleaning system for contact lenses comprising a first component containing a peroxo compound and an alkyl glucoside and a second component containing an $H_2O_2$-neutralilzing agent and a buffer salt in an amount sufficient to adjust the pH of an aqueous contact lens solution containing the first and second components to about 7.

23 Claims, No Drawings

DISINFECTING AND CLEANING SYSTEM FOR CONTACT LENSES

BACKGROUND OF THE INVENTION

1. Field of the Invention

This invention relates to a disinfecting and cleaning system for contact lenses using a peroxo compound.

2. Statement of Related Art

The increasing number of wearers of soft or hard contact lenses necessitates the provision of a system of sterilizing and cleaning preparations which is both convenient and safe to use. Peroxo compounds which destroy germs and fungi are mainly used for this purpose, although any excesses thereof must be destroyed again before the lenses are replaced on the pupil.

Thus, CA U.S. Pat. No. 1,099,885 uses a redox system, for example of ascorbic acid and alkali percarbonate showing a strongly alkaline reaction in aqueous solution, for disinfecting and cleaning contact lenses, the contact lenses being placed in an aqueous solution of this redox system for about 5 minutes. After disinfection, the lenses are optionally rinsed with sodium chloride solution. They may then be replaced on the eyes.

According to published German application no. 33 29 922, contact lenses are disinfected and cleaned by placing them for 10 to 20 minutes in a solution of sodium chloride and a tablet (A) of urea peroxohydrate dissolved therein, then leaving them for 15 minutes in a fresh solution of sodium chloride and a tablet (B) for sodium ascorbate or a mixture of ascorbic acid and sodium carbonate dissolved therein and, finally, placing the lenses in a pure sodium chloride solution for at least 5 minutes. The lenses are then ready to be worn again.

U.S. Pat. No. 4,585,488 describes a process for disinfecting and cleaning contact lenses, in which the contact lenses are first placed for about 20 minutes in a hydrogen peroxide solution to which a catalase tablet is then added to decompose excesses of $H_2O_2$. The enzyme acts within 5 minutes.

Hitherto, the most convenient system for the user has apparently been a disinfecting and cleaning system in which, for example, urea peroxohydrate in a sodium chloride solution is used together with a cationic, nonionic or, preferably, an amphoteric or anionic surfactant, and a catalyst for the subsequent destruction of the peroxide excess. A system such as this is described in U.S. Pat. No. 4,414,127. The separately packed components of the system, namely the urea peroxohydrate on the one hand and a solution of the surfactant, the catalyst and the sodium chloride on the other hand, are combined immediately before use. The user then has nothing further to do. The disadvantage here is that, although basically any surfactant may be used, it is said to be preferred to use two anionic or cationic surfactants selected from very special groups. In addition, a heavy metal salt, such as copper sulfate for example, is used as catalyst for the decomposition of excess urea peroxohydrate. However, the use of heavy metal salts is controversial and in many countries is legally regulated, e.g. on a regional basis in Germany (cf. the various wastewater laws of the individual Federal provinces). Nevertheless, treatment of the lenses still takes up to 4 hours.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that disinfecting and cleaning systems for hard and soft contact lenses which contain solid peroxo compounds, and $H_2O_2$-neutralizing agents, and optionally catalysts and surfactants, and which are also convenient to use can be obtained if the peroxo-containing component ("component A") contains an addition of an alkyl glucoside, and the $H_2O_2$-neutralizing component ("component B") contains an addition of buffer salts to adjust the pH to about 7.

Surprisingly, the disinfecting effect of hydrogen peroxide or $H_2O_2$-yielding peroxo compounds, such as for example potassium persulfate and, preferably, urea peroxohydrate, which show an acidic reaction in aqueous solution, is distinctly improved by the addition of an alkyl glucoside.

Suitable alkyl glucosides for use in the practice of the invention are those corresponding to the general formula $R_1O(C_nH_{2n}O)_y(Z)_x$ where $R_1$ is a $C_8$–$C_{18}$ and preferably a $C_{12}$–$C_{14}$ alkyl chain, $n=2$ or 3, $y=0$ to 10, preferably 0, Z is glucose, and $x=1$ to 10 and preferably 1 to 5. The $R_1$ group can be a straight chain or branched chain alkyl group.

These alkyl glucosides are additionally distinguished by their excellent compatibility with the mucous membrane of the eyes and by their surface-active properties. They may advantageously be combined with other compatible surfactants. By "compatible surfactants" are meant nonionic surfactants of the type which do not neutralize the performance-enhancing antimicrobial properties, for example, compatible surfactants include fatty alcohol ethoxylates, adducts of ethylene oxide and propylene oxide with fatty alcohols or fatty alcohol ethoxylates blocked by terminal n-alkyl groups. These surfactants act to control the cloud point of the cleaning and disinfecting solution and also provide foam-damping properties.

Auxiliaries are preferably added to the peroxo-containing component of the disinfecting and cleaning system, particularly those which adjust the pH during cleaning to a value of from 2 to 7 and preferably to a value of 3.5, such as citric acid, salicylic acid, lactic acid, or mixtures thereof. These auxiliaries act to further enhance the antimicrobial activity of the solution to a considerable extent.

The alkyl glucosides are mechanically mixed with the powderform peroxo compounds, the ratio of the molecular weight of the peroxo compound to the alkyl glucoside being from $1 \times 10^2:1$ to $32 \times 10^4:1$, preferably from $1 \times 10^3:1$ to $32 \times 10^3:1$ and more preferably from $1 \times 10^3:1$ to $8.3 \times 10^3:1$.

The quantities of $H_2O_2$ which are not used in the disinfecting and cleaning process are neutralized by the slightly delayed or even simultaneous addition of reducing agents and/or catalysts (component B). Suitable reducing agents are, for example, ascorbic acid, sodium ascorbate or glucose. Enzymes that destroy $H_2O_2$ are used as catalysts. One particularly suitable and preferred enzyme is catalase. The activity of the catalase is expressed in units/mg. Starting from a concentration of 10.3 mmoles/ml in the reaction mixture, 1 sigma unit degrades 1 mmole $H_2O_2$ in 1 minute at pH 7/25° C. The determination is carried out by measurement of the absorption at 240 nm.

Where only reducing agents are used in component B, they have to be used in at least equimolar quantities in relation to the peroxo compound. However, this may result in too much heat being generated during neutralization which could have a damaging effect on the lenses. Where only catalysts, i.e. enzymes, are used in component B, the neutralization of the residual $H_2O_2$ proceeds quickly, but only at room temperature, and the advantages of heat generation are lost. For this reason, a combination of a reducing agent with catalase has proven to be favorable for neutralization, because in that case the cleaning solution is slightly heated as neutralization begins and heat favorably affects the time taken by the process and the cleaning effect, for example in regard to the removal of fats.

Where only reducing agents are used in component B, the quantity in which they are used corresponds to the quantity of peroxo compound used in component A, i.e. equimolar quantities are used plus an excess of from 1 to 5 and preferably of from 2 to 4 mole % of reducing agent. Where reducing agent is used together with an enzyme, the quantity of reducing agent may be reduced to between about one half to about one quarter of the preceding quantities.

Depending on its activity, the enzyme is used in quantities that provide from 0.001 to 0.2 mg/ml of the in use solution of component A and preferably in quantities of from 0.005 to 0.1 mg/ml of solution, with the quantity chosen depending on the quantity of peroxo compound used.

In addition to the reducing agent and the enzyme, the neutralizing agent of the invention (component B) for the reduction of the $H_2O_2$ residues of the disinfecting and cleaning system also contains buffer salts which adjust the pH value of the solution as a whole to about pH 7, such as sodium hydrogen carbonate, sodium carbonate, or sodium citrate. The disinfecting and cleaning system may also contain the compatible surfactants already discussed above and/or additional salts, such as sodium chloride for example, and/or dyes.

The constituents of the disinfecting and cleaning system according to the invention may be present in aqueous solution, in powder form, or in tablet form. Preferred formulations are the tablet forms. It is important to ensure that the peroxo compound does not come into direct contact with the surfactant and the neutralizing agent mixture during the period of storage. The packs used must be air-tight and, above all, moisture-proof to avoid premature decomposition of the peroxo compound.

If the system of the invention is produced in tablet form, other tabletting aids have to be added. Rapid dissolution may be promoted by the use of disintegrating agents, such as for example cellulose ethers or derivatives, polyethylene glycols, polyvinyl alcohols, and polyvinyl pyrrolidone.

In order slightly to delay the solubility of the neutralizing agent mixture where all the constituents are combined at the same time, the neutralizing agent mixture (component B) is preferably sprayed with water-soluble film-forming polymers which largely cover the constituents of the mixture and must first themselves dissolve before the water reaches the reacting substances. Mixtures "sealed" in this way can also be tabletted.

Water-soluble film-forming polymers that can be used herein include polymers of acrylic acid and/or methacrylic acid that are water soluble, e.g. those having a medium molecular weight in the range of from 50,000 to 500,000. Generally, from 0.5 to 50 mg, preferably from 10 to 20 mg, of polymer per gram of component B is employed, depending on the thickness of the coating desired, i.e. in general the greater the thickness of the coating the longer the delay before dissolution.

The system according to the invention is preferably formulated in the form of tablets. In this case, the contact lens cleaning container can be filled with the disinfecting composition and the neutralizing mixture at the same time, for example by using two individual tablets wherein the tablet containing the neutralizing mixture dissolves with delay in water or sodium chloride solution, and the tablet containing the disinfecting composition dissolves quickly therein. However, two different powders or mixed powder/tablet formulations for simultaneous or sequential use are also very safe for the contact lens wearer to use. In addition, possible confusion can be avoided by dyeing the disinfecting and neutralizing components different colors. Where the advantageous tablet formulations of the invention are used, reduction takes place immediately after disinfection and cleaning without any need for any further action on the part of the contact lens wearer.

In using the system of the invention, component A is added to water or sodium chloride solution in sufficient quantity to provide an aqueous solution containing from 0.1 to 15% by weight, preferably from 0.5 to 10% by weight, and most preferably from 4 to 6% by weight of $H_2O_2$ therein.

The disinfection and cleaning process is carried out at temperatures of from 10° to 60° C. and preferably at a temperature of around 35° C. in a glass or any other suitable container. On the one hand, these temperatures may be self-generating as reduction begins and may favorably influence the cleaning effect; on the other hand disinfection, cleaning and also reduction can take place at elevated temperature if the solution is heated from an external heat source. In the latter case, the content of reducing agent in the neutralizing agent mixture can be further reduced, so that the enzyme alone is largely responsible for degradation of the excess $H_2O_2$.

It is pointed out that, in the context of the invention, "neutralization" is intended to mean the destruction of excess $H_2O_2$. The agents used for this purpose have been called "neutralizing agents".

Experimental Section

The following Examples with the test results cited therein, which are given for illustrative and not limiting purposes, show the advantages of the disinfecting and cleaning system according to the invention for contact lenses over the prior art as represented by U.S. Pat. No. 4,414,127.

(I.) Disinfecting effect

The disinfecting effect was determined by the quantitative suspension test according to the periodically modified guidelines of the deutsche Gesellschaft fur Hygiene und Mikrobiologie (Zbl. Bakt. Hyg., 1. Abt. Orig. B 172 (1981) 534) using the following microorganisms:

1. *Staphylococcus aureus*
2. *Pseudomonas aeruginosa*
3. *Candida albicans*
4. *Asperigillus niger*

To this end, 0.1 ml was taken from a microorganism suspension containing approximately $10^8$ microorganisms/ml and added to 10 ml of the disinfecting and cleaning solution according to the invention so that the test concentration was at about $10^6$ microorganisms/ml. Disinfection is said to have taken place when a microorganism reduction of $10^5$ microorganisms or 5 log stages is obtained. The test concentration and choice of the test microorganisms also correspond to the stipulations of the British Pharmacopoeia 1980, Addendum 1982, Appendix XVI.

(II.) Cleaning effect

To test the cleaning effect, contact lenses differing in their material composition were artificially soiled using the following three soil types:
(a) Fatty soil
(b) Protein soil
(c) Inorganic soil (a) Fatty soil The fatty soil consisted of the following constituents (per 100 g solution):
0.010 g tripalmitin
0.100 g triolein
0.100 g trilinolein
0.005 g cholesteryl palmitate
0.035 g cholesteryl oleate
0.050 g cholesteryl linoleate The lipids were weighed in and first melted with one another before being made up to 100 g with distilled water. Quantities of 3 ml were taken from the solution to pour over contact lenses. The solution was then concentrated almost to dryness over a period of about 16 hours at 35° C., the lipids being deposited on the surface of the contact lenses as non-rinsable soil.

(b) Protein soil 0.04 g mucin
0.18 g albumin
0.08 g a-globulin
0.08 g b-globulin
0.08 g g-globulin
0.18 g lysozyme The proteins were first predissolved in sodium chloride solution and the resulting solution subsequently made up to 100 g with distilled water. The soil was deposited on a contact lens in the same way as described in (a); in addition, the deposit was irradiated for 30 minutes with UV-light.

(c) Inorganic soil

The inorganic soil was prepared as follows:
Solution 1
1.25 g $Na_2HPO_4$, 0.975 g $NaH_2PO_4$, and 1.09 g $NaHCO_3$ were dissolved in 100 g distilled water.
Solution 2
0.065 g $CaCl_2$ were likewise dissolved in 100 g distilled water.

The contact lenses were soiled by dipping a contact lens in a mixture of 2.9 ml of solution 1 and 0.1 ml of solution 2 and producing a non-rinsable soil in the same way as described in (a).

The tapwater used for the tests had the following quality:
$Ca^{2+}$: 2.12 moles/m$^3$
$Mg^{2+}$: 0.46 mole/m$^3$
$Na^+$: 3.44 moles/m$^3$
$K^+$: 0.12 mole/m$^3$
$Zn^{2+}$: 0.3 mmole/m$^3$
$Fe^{2+}$: 0.9 mmole/m$^3$
$Cu^{2+}$: 0.0 mmole/m$^3$
$Mn^{2+}$: 0.4 mmole/m$^3$
Si: 0.14 mole/m$^3$
$Cl^-$: 3.78 moles/m$^3$
$SO_4^{2-}$: 0.67 mole/m$^3$
pH value 7.4
Conductivity 92 mS/m

EXAMPLE 1

1.5 g of urea peroxohydrate, 1 mg of a $C_{12}$–$C_{14}$ alkyl glucoside with x=1.4, 2 mg of a nonionic surfactant consisting of the reaction product of 1 mole of a $C_{12}$–$C_{14}$ fatty alcohol mixture and 9 moles of ethylene oxide etherified with 1 mole of butyl alcohol and 0.13 g of citric acid were dissolved in 10 ml of distilled water. A hydrogen peroxide concentration of 5% by weight was obtained in the solution at a pH value of 3.5.

In the quantitative suspension test using *Staphylococcus aureus*, a bacteria reduction of 6 log stages was obtained after only 2 minutes. The same results were also obtained in the absence of the additional nonionic surfactant. The completely surfactant-free solution only reached this antimicrobial activity level after 7.5 minutes. The addition of the conventional nonionic surfactant alone did not shorten this time. This Example demonstrates the improvement in the germicidal effect of the solution after the addition of very small quantities of alkyl glucoside.

EXAMPLE 2

When the alkyl glucoside in Example 1 was replaced by the surfactant used in accordance with U.S. Pat. No. 4,414,127, namely Miranol ® C2M conc., a product of Miranol Chemical Corp., a bacteria reduction of 6 log stages was only achieved after 4 minutes in the quantitative suspension test using the same test bacteria.

Thus, although an increase in performance—also offered as a "reward" in the prior art—was observed in relation to the surfactant-free solution, the increase in performance according to the invention in Example 1 is much more clearly pronounced.

Another advantage over the prior art is the very low surfactant concentration according to the invention. Much higher surfactant concentrations, namely beyond 0.1% by weight, but preferably 1%, are disclosed in U.S. Pat. No. 4,414,127.

EXAMPLE 3

When the alkyl glucoside in Example 1 was replaced by an oxo alcohol ethoxylate (for example isotridecanol×9 moles ethylene oxide=Marlipal 013/90 ™, a product of Huls A.G.), a bacteria reduction of 6 log stages is again achieved only after 4 minutes for the same test conditions.

EXAMPLE 4

When the alkyl glucoside in Example 1 was replaced by a condensate of ethylene oxide and propylene oxide (Pluronic L 61 ®, a product of Wyandotte), a bacteria reduction of 6 log stages was only achieved after 5 minutes under the same test conditions.

Examples 1 to 4 thus illustrate the significant advantages of the surfactants of the invention over the prior art surfactants and other nonionic surfactants.

EXAMPLE 5

0.03 g salicylic acid was additionally dissolved in the solution of Example 1. The disinfection rate as determined by the quantitative suspension test was again increased. Using Staphylococcus aureus as the test bacteria, the time taken to achieve the desired bacteria reduction of 6 log stages was shortened by 1 minute.

Candida albicans was deactivated (5 log stages) after a contact time of 5 minutes with the solution of Example 1. The same disinfection level was achieved after only 3 minutes by addition of salicylic acid.

Pseudomonas aeruginosa was deactivated (6 log stages) after only 30 seconds by the solution of Example 1; an increase in performance according to Example 5 could not be measured.

EXAMPLE 6

The quantitative suspension test was also carried out at an elevated temperature (35° C.).

The results obtained with the solutions of Examples 1 and 5 show that an increase in temperature to 35° C. results in a further reduction in the disinfection time.

EXAMPLE 7

Contact lenses were contaminated for 5 minutes with a microorganism mixture consisting of 2 drops of each of the microorganisms *Staphylococcus aureus, E. coli, Pseudomonas aeruginosa* and *Candida albicans* (microorganism count $7 \times 10^8$) and dried for 10 minutes on sterile filter paper. The lenses were then disinfected at room temperature in a Petri dish containing 10 ml of the products according to Examples 1 and 5. The contact lenses were completely decontaminated after 5 minutes at room temperature.

EXAMPLE 8

As in Example 7, contact lenses were contaminated for 5 minutes with Aspergillus niger in a microorganism suspension consisting of $3 \times 10^7$ microorganisms.

Using a solution according to Example 5, the contact lenses were again decontaminated after 5 minutes at room temperature.

EXAMPLE 9

Contact lenses were soiled as described with deposits (a), (b) and (c) and then cleaned with solutions according to Examples 1 and 5.

The cleaning effect was evaluated using a Zeiss SV 8 stereomicroscope.

Fatty deposits were removed by the alkyl glucoside in approximately 5 minutes. The corresponding surfactant-free solution showed a distinctly poorer effect.

Protein deposits were also removed in approximately 5 minutes. This eliminated the need for the otherwise necessary weekly intensive cleaning.

Inorganic deposits were completely removed from the lenses in 2 minutes through the mildly acidic character of the solutions.

EXAMPLE 10

Contact lenses were cleaned at 35° C. as in Example 9. The advantages of a shorter cleaning time were observed in particular in the removal of fatty deposits.

EXAMPLE 11

A tablet consisting of 1.5 g of urea peroxohydrate, 1 mg of $C_8$-$C_{10}$ alkyl glucoside with x=1.8, 2 mg of nonionic surfactant (as in Example 1), 0.13 g of citric acid, 0.03 g of salicylic acid and 0.05 g of sodium chloride was placed in a cleaning container together with 10 ml of a 0.9% sodium chloride solution and the contact lenses to be cleaned.

The tablet dissolved in about 2 minutes. Disinfection and cleaning were over after 5 minutes. Another tablet consisting of 0.6 mg of catalase (10,000–25,000 sigma units/mg), 0.38 g of sodium ascorbate, 0.25 g of sodium hydrogen carbonate, 33 mg of polyethylene glycol, molecular weight 6000 (Polywachs 6000 ®), and 2 mg of a condensate of a $C_{16}$-$C_{18}$ fatty alcohol and 20 moles of ethylene oxide (Eumulgin B2 ®) was then placed in the container.

This second tablet dissolved in about 3 minutes, neutralized excess peroxide and, at the same time, established a pH value of around 7. The cleaned contact lenses were then removed from the container, rinsed under running tapwater and were then compatible with the eyes again.

In a modified test, the treated contact lenses were briefly immersed in isotonic sodium chloride solution instead of being rinsed with running tapwater before they were replaced by the wearers. There were no complaints of incompatibility.

EXAMPLE 12

In continuation of Example 11, 0.01 g of EDTA, disodium salt, was incorporated in the first tablet in addition to the constituents already described.

This first tablet was then placed in a cleaning container together with 10 ml of tapwater and the contact lenses to be cleaned. After the tablet had dissolved, the contact lenses were disinfected and cleaned in about 5 minutes. Neutralization was obtained as described in Example 11.

EXAMPLE 13

A powder mixture consisting of 1.5 g of urea peroxohydrate, 1 mg of alkyl glucoside (as in Example 1), 2 mg of nonionic surfactant (as in Example 1), 0.13 g of citric acid and 0.03 g of salicylic acid was taken from a gas tight and moisture proof bag and placed together with the contact lenses to be cleaned in a cleaning container filled with 10 ml of distilled water. The powder dissolved very quickly. Disinfection and cleaning were over in about 5 minutes. Neutralization was obtained as described in Example 11.

EXAMPLE 14

A tablet consisting of 1.5 g of urea peroxohydrate, 1 mg of alkyl glucoside, 2 mg of mixed ether, 0.05 g of sodium chloride, 0.13 g of citric acid and 0.03 g of salicylic acid, and a second tablet consisting of a mixture of 0.36 g of sodium ascorbate, 0.6 mg of catalase (10,000–25,000 sigma units/mg), 0.24 g of sodium hydrogen carbonate and 0.032 g of Polwachs 6000 ®, onto which 9 mg of a neutralized polyacrylate had been sprayed before compression, were placed in a container together with the soiled contact lenses and 10 ml isotonic sodium chloride solution. The first tablet dissolved in about 3 minutes and formed the solution required for disinfection and cleaning.

By virtue of the presence of polyacrylate, which coated most of the individual constituents of the mixture, the second tablet dissolved with a slight delay in about 12 minutes, reducing the excess quantities of peroxide and establishing a pH value of 7.

The cleaning solution was poured out and, after immersion in an isotonic sodium chloride solution, the contact lenses were replaced on the eyes without causing any discomfort.

EXAMPLE 15

For the same composition as in Example 14, the constituents of the first tablet were initially introduced in powder form and used in combination with the second tablet described in Example 14. As expected, the results were the same as in Example 14.

We claim:

1. In a two component disinfecting and cleaning system for contact lenses which comprises a first component containing a peroxo compound, and a second component containing a $H_2O_2$-neutralizing agent, the improvement wherein the first component contains a solid peroxo compound and an alkyl glucoside wherein the molar ratio of peroxo compound to alkyl glucoside is from about $1 \times 10^2:1$ to about $32 \times 10^4:1$, and wherein the second component contains as the $H_2O_2$-neutralizing agent in a reducing agent and/or a catalyst and at least one buffer salt in amount sufficient to adjust the pH of an aqueous contact lens solution containing the first and second components to about 7.

2. The system of claim 1 wherein the peroxo compound is potassium persulfate or urea peroxohydrate.

3. The system of claim 1 wherein the alkyl glucoside has the formula $$R_1O(C_nH_{2n}O)_y(Z)_x$$

wherein $R_1$ is a $C_8$–$C_{18}$ alkyl group, n=2 or 3, y=0 to 10, Z is glucose, and x=1 to 10.

4. The system of claim 3 wherein $R_1$ is a $C_{12}$–$C_{14}$ alkyl group.

5. The system of claim 3 wherein y=0.

6. The system of claim 3 wherein x=1 to 5.

7. The system of claim 3 wherein $R_1$ is a $C_{12}$–$C_{14}$ alkyl group, y=0, and x=1 to 5.

8. The system of claim 1 wherein the first component also contains a nonionic surfactant compatible therewith.

9. The system of claim 1 wherein the pH of the solution containing the first component only is in the range of from about 2 to about 7.

10. The system of claim 9 wherein the pH is about 3.5.

11. The system of claim 1 wherein the ratio is from about $1 \times 10^3:1$ to about $32 \times 10^3:1$.

12. The system of claim 11 wherein the ratio is from about $1 \times 10^3:1$ to about $8.3 \times 10^3:1$.

13. The system claim 1 wherein the reducing agent is ascorbic acid, sodium ascorbate, or glucose.

14. The system of claim 1 wherein the catalyst is an enzyme.

15. The system of claim 1 wherein both a reducing agent and a catalyst are present and the catalyst is an enzyme.

16. The system of claim 14 wherein the enzyme is catalase.

17. The system of claim 1 wherein the system is in the form of an aqueous solution.

18. The system of claim 1 wherein the first component is in powder form or tablet form, and the second component is independently in powder form or tablet form.

19. The system of claim 1 wherein the $H_2O_2$-neutralizing agent is coated with a water soluble film-forming polymer.

20. The system of claim 19 wherein the water soluble film-forming polymer is a polymer of acrylic acid and/or methacrylic acid.

21. A method for disinfecting and cleaning a contact lens comprising contacting said contact lens with an acidic aqueous solution of the first component of the system of claim 19 which also contains the second component of the system of claim 19.

22. A method for disinfecting and cleaning a contact lens comprising contacting said contact lens with an aqueous solution of the first component of the system of claim 1 followed by the addition of the second component thereof to the aqueous solution of the first component.

23. In a two-component one step disinfecting and cleaning system for contact lenses which comprises a first component containing a peroxo compound and a second component in powder or tablet form containing an $H_2O_2$-neutralizing agent, the improvement wherein the second component is coated with a water soluble film-forming polymer, wherein the $H_2O_2$-neutralizing agent is a reducing agent and/or a catalyst, wherein the second component contains at least one buffer salt in amount sufficient to adjust the pH of an aqueous contact lens solution containing the first and second components to about 7, and wherein the first component contains an alkyl glucoside and a solid peroxo compound.

* * * * *